(12) United States Patent
Tuncay et al.

(10) Patent No.: US 6,879,712 B2
(45) Date of Patent: Apr. 12, 2005

(54) SYSTEM AND METHOD OF DIGITALLY MODELLING CRANIOFACIAL FEATURES FOR THE PURPOSES OF DIAGNOSIS AND TREATMENT PREDICTIONS

(76) Inventors: Orhan C. Tuncay, 210 Locust St., Apt. 28G, Philadelphia, PA (US) 19106; John C. Slattery, 3221 Crescent Rim, Boise, ID (US) 83706

( * ) Notice: Subject to any disclaimer, the term of this patent is extended or adjusted under 35 U.S.C. 154(b) by 577 days.

(21) Appl. No.: 09/864,808

(22) Filed: May 25, 2001

(65) Prior Publication Data

US 2002/0176612 A1 Nov. 28, 2002

(51) Int. Cl.[7] .............................. G06K 9/00
(52) U.S. Cl. ................. 382/128; 128/922; 345/630
(58) Field of Search ...................... 382/115, 118, 382/154, 195, 197, 254, 203, 276; 345/425, 435

(56) References Cited

U.S. PATENT DOCUMENTS

| | | | |
|---|---|---|---|
| 5,659,625 A | | 8/1997 | Marquardt ............... 382/118 |
| 5,867,588 A | | 2/1999 | Marquardt ............... 382/118 |
| 5,882,192 A | * | 3/1999 | Bergersen ................. 433/2 |
| 5,951,571 A | | 9/1999 | Audette .................. 606/130 |
| 5,960,099 A | * | 9/1999 | Hayes et al. ............. 382/118 |
| 6,015,289 A | | 1/2000 | Andreiko et al. ........... 433/3 |
| 6,081,739 A | * | 6/2000 | Lemchen ................. 600/407 |
| 2001/0002310 A1 | * | 5/2001 | Chishti et al. ............ 433/24 |
| 2001/0027271 A1 | * | 10/2001 | Franck et al. ............ 600/426 |
| 2002/0012454 A1 | * | 1/2002 | Liu et al. ............... 382/118 |

* cited by examiner

*Primary Examiner*—Samir Ahmed
*Assistant Examiner*—Anand Bhatnagar
(74) *Attorney, Agent, or Firm*—LaMorte & Associates

(57) ABSTRACT

A system and method for generating and utilizing a computer model of the craniofacial features of a patient is claimed. To create the computer model, three-dimentional data regarding the patient's facial features, dental features and skeletal features is collected. Data regarding facial features is acquired using laser scanning and digital photograph. Data regarding dental features are acquired by physically modeling the teeth and laser scanning the models. Lastly, data regarding the skeletal features is obtained from radiographs. The data are combined into a single computer model that can be manipulated and viewed in the three-dimensions. The model also has the ability to be animated between the current modeled craniofacial features and theoretical craniofacial features.

15 Claims, 5 Drawing Sheets

SYSTEM AND METHOD OF DIGITALLY MODELLING CRANIOFACIAL FEATURES FOR THE PURPOSES OF DIAGNOSIS AND TREATMENT PREDICTIONS

BACKGROUND OF THE INVENTION

1. Field of the Invention

In general, the present invention relates to systems and methods that are used to diagnose craniofacial deformities and predict outcomes to various treatments for those deformities. More particularly, the present invention relates to computer imaging and modeling systems that are used to create and manipulate craniofacial images.

2. Description of the Prior Art

The craniofacial characteristics of each person are unique, thereby defining a person's appearance. However, due to genetics, some people are born with undesired craniofacial features or craniofacial deformities. Furthermore, in this dangerous world, many people incur injuries to there craniofacial features that must be treated.

The task of treating craniofacial trauma, correcting craniofacial deformities and altering undesired craniofacial features typically fall into the practice of orthodontists, oral surgeons and plastic surgeons, depending upon the type of corrective measures required.

When a surgeon or orthodontist alters the craniofacial features of a patient, the appearance of the patient may change. Both physicians and patients are very weary of this change. Often, the change to the craniofacial features can be anticipated. For example, when a patient has a few crooked teeth straightened, the physician and patient alike can easily visualize the patient's appearance. However, other procedures are not so easily visualized. If a patient is having jaw surgery, a rhinoplasty or other such procedure, both the physician and the patient want to visualize the change prior to undergoing the operation. The physician needs to visualize the anatomical change for the purposes of diagnosis. The patient wants to visualize the change because it is his/her appearance that is to be altered.

The prior art is replete with systems that help physicians and patients predict the changes that will occur in a patient's anatomy and appearance as a result of craniofacial surgery. Many such systems are currently commercially available and are sold under trade names, such as Quick Ceph, Dentofacial Planner, Orthovision, Dolphin Imaging and the like.

However, the craniofacial features of a person are three-dimensional. Most all the commercially available systems for imaging craniofacial features only provide two-dimensional images. As such, these prior art systems only enable physicians and patients to view changes in the profile view. Such predictions are useful but are not sufficient to truly visualize a changes that may occur after a craniofacial procedure. Some systems have been developed that attempt to provide imaging in three dimensions. Such systems are exemplified by U.S. Pat. No. 6,081,739 to Lemchen, entitled Scanning Device Or Methodology To Produce An Image Incorporating Correlated Superficial Three Dimensional Surface And X-Ray Images And Measurements Of An Object; U.S. Pat. No. 5,867,588 to Marquardt, entitled Method And Apparatus For Analyzing Facial Configurations And Components; and U.S. Pat. No. 5,659,625 to Marquardt, also entitled Method And Apparatus For Analyzing Facial Configurations And Components. A problem with such prior art three-dimensional systems is their inability to accurately map external facial appearance with both the skeletal structure of the patient and the dental structure of the patient in a single image.

A need therefore exists for an improved method and system for creating three-dimensional models of a patient, that accurately includes external facial features, skeletal features and dental features, wherein that model can be virtually altered for diagnostic and treatment outcome purposes. This need is met by the present invention as described and claimed below.

SUMMARY OF THE INVENTION

The present invention is a system and method for generating and utilizing a computer model of the craniofacial features of a patient. To create the computer model, three-dimentional data regarding the patient's facial features, dental features and skeletal features is collected. Data regarding facial features is acquired using laser scanning and digital photographs. Data regarding dental features are acquired by physically modeling the teeth and laser scanning the models. Lastly, data regarding the skeletal features is obtained from radiographs. The data is combined into a single computer model that can be manipulated and viewed in the three-dimensions. The model also has the ability to be animated between the current modeled craniofacial features and theoretical craniofacial features. In this manner, the computer model can be used to diagnose abnormalities, and approximate physiological changes that may occur because of corrective surgery, braces, aging and/or growth.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE INVENTION

The present invention is a system and method for generating a digital representation of the craniofacial features of a patient, wherein the digital representation includes exact skeletal features, dental features and soft tissue facial features. The digital representation can then be altered and/or animated. By having the ability to alter and/or animate the digital representation, a process is created that is highly useful in diagnosing craniofacial problems and visualizing physical changes that can be created by various types of treatments.

Figure 1:
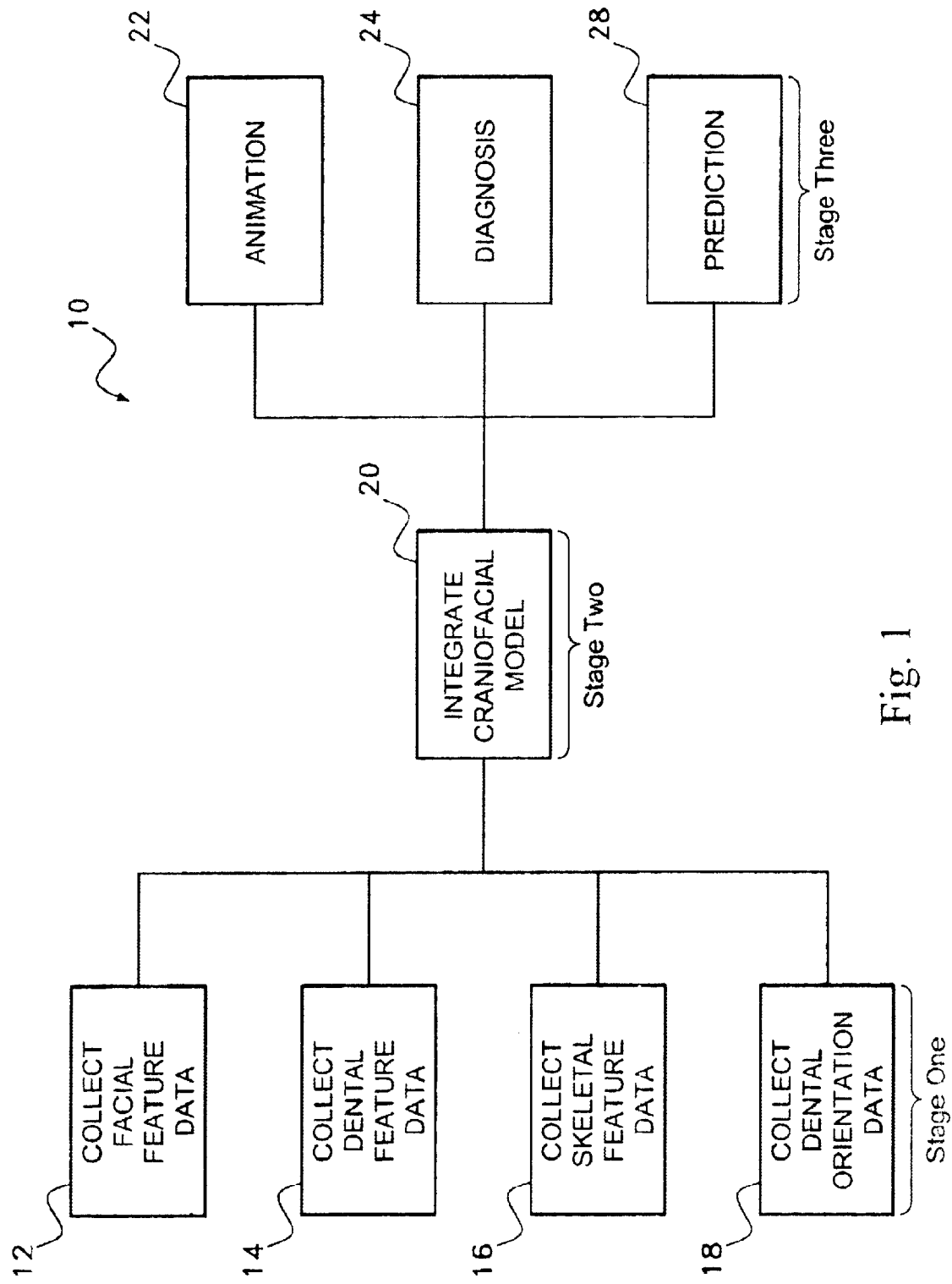
FIG. 1 is a block diagram schematic of the overall modeling system and method in accordance with the present invention.

Referring to FIG. 1, it can be seen that the present invention system and method 10 contains three stages. The first stage is the data collection stage. During the data collection stage, data of a patient's craniofacial features is collected. As is indicated by Block 12, facial feature data is collected that is representative of the external appearance of the soft tissue components of a patient's face. As is indicated by Block 14, dental feature data is collected that is representative of the condition and orientation of that patient's teeth. As is indicated by Block 16, data is also collected on the skeletal features of the patient. Lastly, as is indicated by Block 18, orientation data is collected that is used to orient the dental feature data in the overall craniofacial model. The steps used to collect the various types of data are unique and will later be explained in more detail.

Once all the data is collected, the second stage of the system and method 10 is implemented. As is indicated by Block 20, the collected data from stage one is manipulated to create an accurate digital craniofacial model of the patient. As will be later explained, the craniofacial model models a patient's craniofacial features in three dimensions that can be viewed from any vantage point. The manipulation of the collected data in stage two is done in a computer through the use of novel software applications, as will also be later explained The third stage of the system and method 10 is the use of the craniofacial model by a physician or patient. As is indicated by Block 22, the craniofacial model can be animated to illustrate features through a variety of changing expressions. The craniofacial model can also be used to diagnose craniofacial abnormalities, as is indicated by Block 24. The animation of the craniofacial model is very useful in diagnosing abnormalities that manifest themselves when a patient chews, smiles, yawns or otherwise undergoes movement in the craniofacial structure. Furthermore, as is indicated by Block 28, the craniofacial model can be used to predict changes to the craniofacial features created by aging, growth, surgery or orthodontic appliances.

Each of the logic blocks illustrated in FIG. 1 can be multiple process steps. Each of the logic blocks shown in FIG. 1, will therefore be individually described, beginning with the data collection blocks in stage one.

Figures 2, 3:
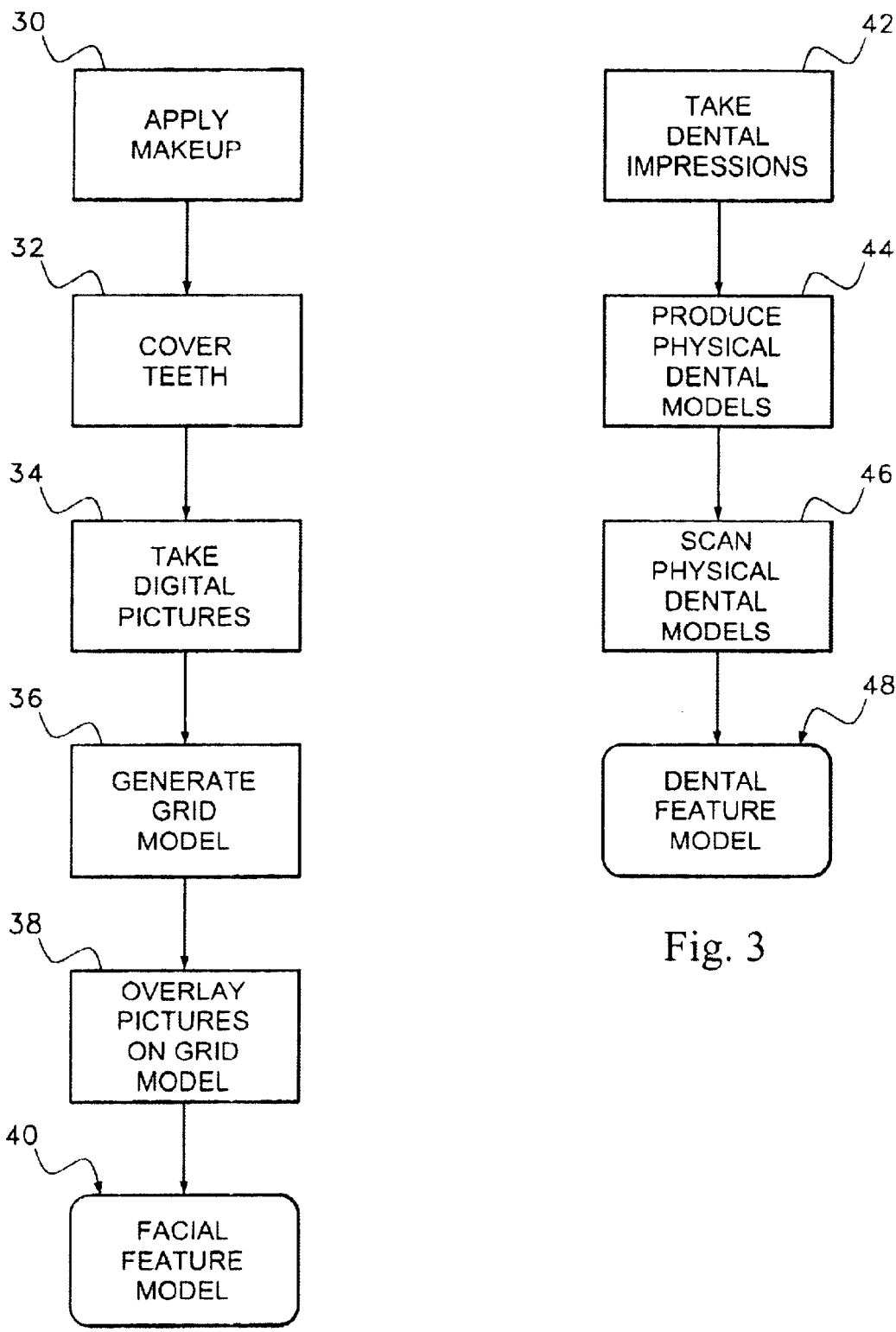
FIG. 2 is a block diagram schematic illustrating the method steps used to collect facial feature data.
FIG. 3 is a block diagram schematic illustrating the method steps used to collect dental feature data.

Referring to FIG. 2, the method of collecting facial data is more specifically described. To collect facial data, low gloss make-up is applied to the face of a patient. See Block 30. The low gloss make-up is desired in order to accurately scan the facial features with a laser scanner. If make-up were not used, shinny points on the skin may distort the scanned image being collected. Furthermore, as is indicated by Block 32, the teeth are covered. The teeth are skinny and reflect laser light. So to prevent distortions in a laser scan, the teeth are covered with a non-reflective material. Orientation points are then marked in the make-up at predetermined points.

Prior to laser scanning the patient's facial features, the patient's face is photographed using a digital camera. This is shown by Block 34. Several pictures may be taken, wherein different pictures are taken at known distances and at known angles relative the primary plane of the patients face. Digital pictures may also be taken of different facial expressions, such as a smile, a grin, an mouth open and the like.

After the digital pictures have been taken, the patient's face is then scanned with a non-contact laser scanner. An example of an appropriate non-contact laser scanner would be the Vivid 700 model laser scanner produced by Minolta. The patient's face is scanned from the same positions and with the same expressions as were the digital picture. In this manner, a laser scan can be associated with a digital picture.

Using the data collected from each laser scan, a model grid framework of the patient's face is generated using commercial software. This is indicated by Block 36 in FIG. 2. For example, if a Vivid 700 laser scanner is used, Vivid 1.3 software can be used to create a model grid framework of the collected data. The orientation points placed on the patient's face are noted on the grid framework. The digital picture corresponding to each laser scan also contains the same orientation points, as does each laser scan. Using the orientation points as references, the digital picture for each laser scan is overlaid over the model grid framework that was generated for that scan. This process is indicated by Block 38 in FIG. 2. This provides facial texture to the collected data. Once the overlays are complete, a first digital model 40 is produced that corresponds to the facial characteristics of a patient. The facial feature model 40 is three-dimensional and contains data points from different perspectives and with different facial expressions.

Referring to FIG. 3, the steps involved in collecting dental feature data are described. To collect dental feature data on a patient, impressions are taken of the patient's teeth using conventional techniques. Block 42 in FIG. 3 shows this process. Three-dimensional physical models of the teeth are then made from the impressions, as is indicated by Block 44. Orientation points are placed on the physical models. Once the physical models are complete, the models are scanned using a non-contact laser scanner. Block 46 indicates this process. A computer model 48 of the patient's dental features is therefore created that represents the patient's actual dental features in three dimensions.

Figure 4:
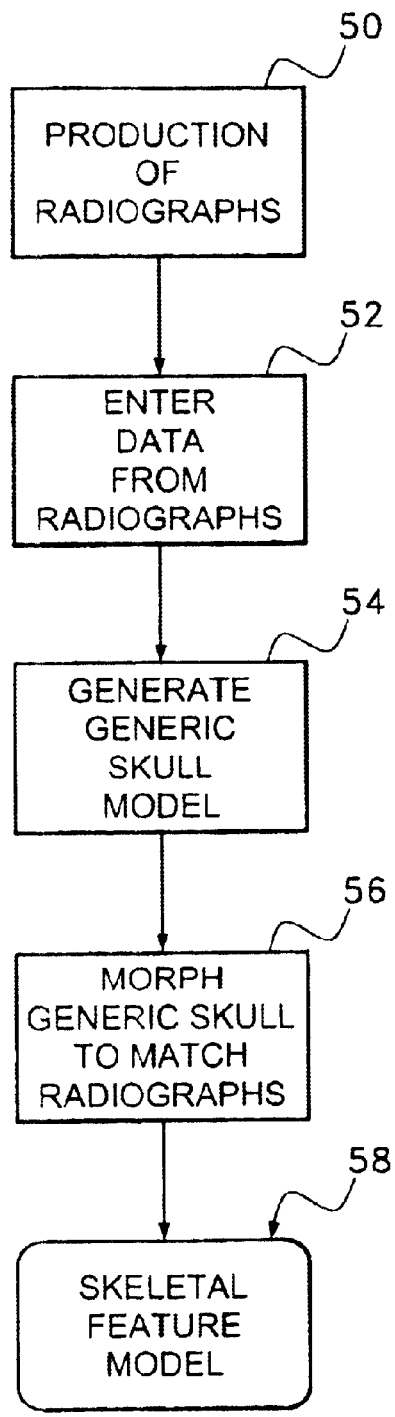
FIG. 4 is a block diagram schematic illustrating the method steps used to collect skeletal feature data.

Referring to FIG. 4, the steps involved in collecting skeletal data are described. To collect skeletal data, lateral and PA radiographs are taken of the skull using traditional radiology techniques. This process is shown by Block 50 in FIG. 4. Data points from the radiographs are then read into a computer, as is indicated by Block 52. Furthermore, as is indicated by Block 54, a generic three-dimensional skull is generated in the computer using commercial software. The data points from the radiographs are then projected around the generic skull. Using commercial software, such as 3D Studio Max, the generic skull computer model can be morphed to match the data points collected from the radiographs. This process is shown by Block 56 in FIG. 4. The result is a computer model 58 of a skull that mimics the actual skull of the patient.

Figure 5:
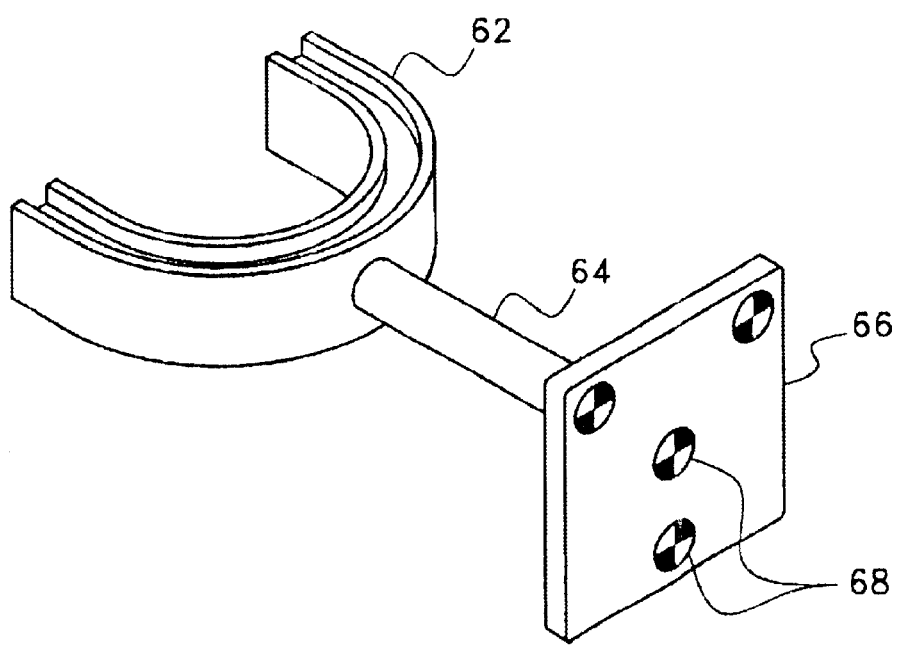
FIG. 5 is a perspective view of an exemplary embodiment of a bite jig.

Referring to FIG. 5, a bite jig 60 is shown that is used in the process of collecting dental orientation data. The bite jig 60 has a bite plate 62 that engages the teeth within the mouth. A shaft 64 extends away from the bite plate 62. The shaft 64 terminates with an orientation plate 66 that has reference points 68 on it.

Figures 6, 7:
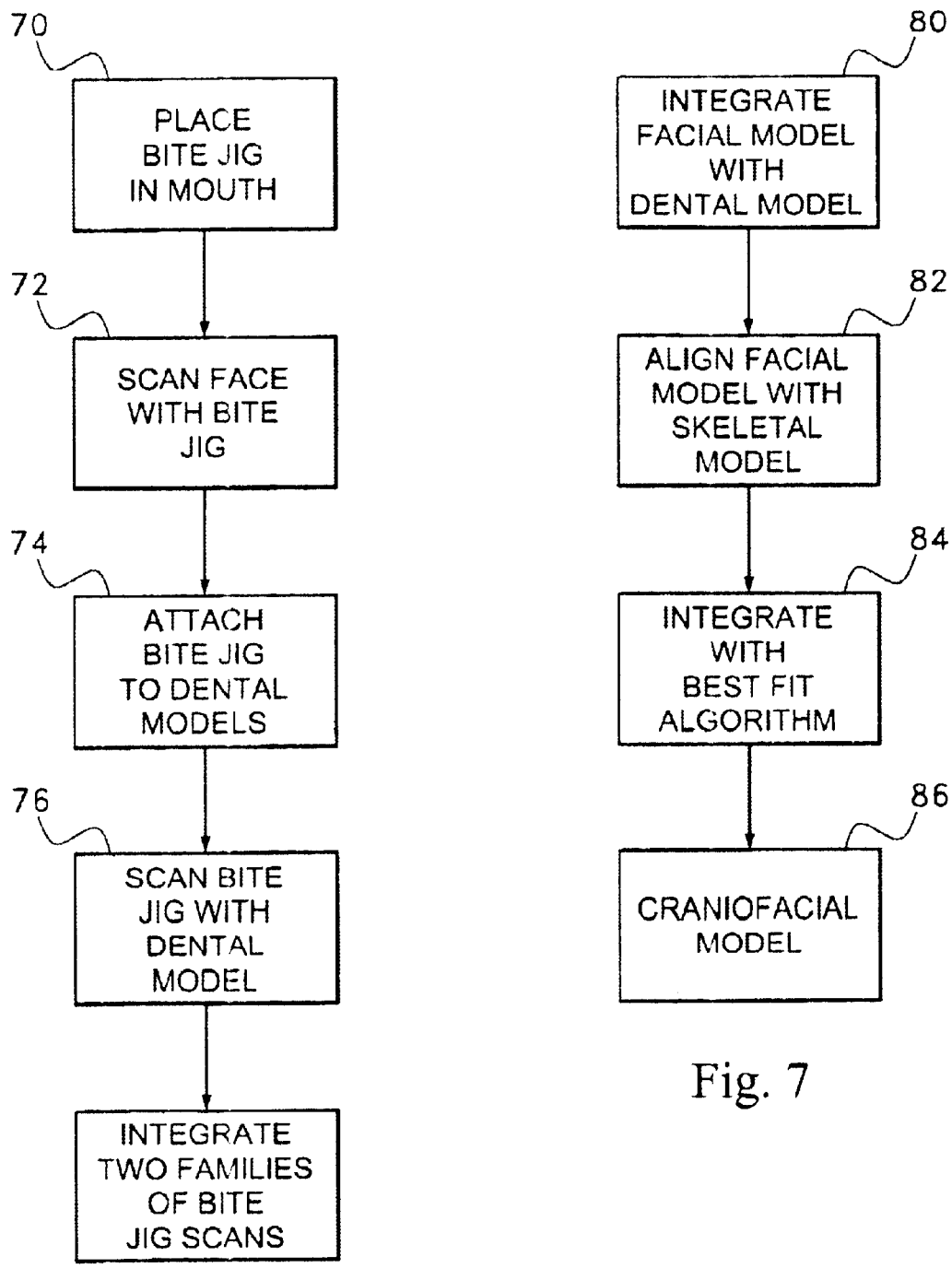
FIG. 6 is a block diagram schematic illustrating the method steps used to collect dental feature orientation data using the bite jig of FIG. 5.
FIG. 7 is a block diagram schematic illustrating the method step used in integrating the craniofacial model from the collected data.

Referring to FIG. 6, the method of collecting dental orientation data with the bite jig 60 (FIG. 5) is described. As is indicated by Block 70, the bite jig is placed in the mouth of the patient and is engaged by the patient's teeth. Once in place, the patient's face is again scanned using the non-contact laser scanner, as is indicated by Block 72. The laser scans, therefore, collect data reference points from the patient's face as well as reference points from the orientation plate 66 (FIG. 5) on the bite jig.

As is indicated by Block 74, the bite jig is then affixed to the physical models of the teeth that have been previously prepared. Once the bite jig is affixed to the models of the teeth, the entire assembly is scanned with the non-contact laser scanner. Block 76 indicates this process. As has been previously mentioned, the physical models of the teeth contain reference points that are detected in the laser scan. The orientation plate 66 (FIG. 5) on the bite jig also contains reference points that are detected by the laser scan. By scanning the model of the teeth engaging the bite jig, the orientation of the bite plate relative to the teeth becomes known.

Returning to FIG. 1, it will now be understood that from stage one of the process, three-dimensional models of the facial features, dental features, and skeletal features become known. See Blocks 12, 14 and 16. Furthermore, the positional relationship between the facial features and the orientation plate of the bite jig are known, as is the positional relationship between the orientation plate of the bite jig and the modeled teeth. See Block 18.

Once this data is collected, stage two begins wherein the collected data is integrated into a single craniofacial model. The integration of the various data models can be done in a number of different ways. Referring to FIG. 7, it can be seen that since the positional relationship of the bite jig's orientation plate 66 (FIG. 5) is known relative to both the facial features and the dental features, the dental features can be oriented with the facial features by simply aligning common points on the orientation plate. The model of the facial features and the model of the dental features therefore integrate into a single model in a simple fashion. This initial integration is shown by Block 80 in FIG. 7. To integrate the skeletal features into the combined facial feature/dental model, the profile of the facial features is aligned over the profile of the modeled skull, as indicated by Block 82. A front view of the facial features is then aligned with a front view of the modeled skull. The alignment is done along the mid-sagittal plane. Once proper alignment is achieved, the skeletal feature model and the facial feature model are integrated using commercially available best-fit algorithms, as is indicated by Block 84.

The result after integration is a single craniofacial model 86 that contains detailed data about a patient's facial features, skeletal features and dental features. The craniofacial model 86 is three-dimensional, thereby producing a three-dimensional digital representation of a patient's craniofacial features.

Now that a three-dimentional representation of a patient's craniofacial structure has been developed, stage three (FIG. 1) can be started. In stage three, it can be seen that the craniofacial model can be used as a tool for medical diagnosis. See block 24 in FIG. 1. Using just a static three-dimentional model, a physician can visualize the asymmetry of dental arches from a coronal perspective. Jaw deformities, nasal deformities and eye socket deformities can also readily be visualized from the model. Furthermore, deformities in the soft tissue of the face can also be visualized.

To assist in diagnosis, the craniofacial model can also be animated, as is indicated by Block 22 in FIG. 1. To animate the model, many types of commercial animation software can be used, provided that software supports digital multi-frame animation. Examples of appropriate software packages are 3D Studio Max and Softimage. As has been previously mentioned, the facial features of the patient are scanned in a plurality of different poses. Using animation algorithms, any existing pose can be animated to morph into any other pose. As such, the model can be animated to smile, frown, chew or undergo any desired craniofacial movement.

The last way to manipulate the craniofacial model is to create artificial conditions and morph the craniofacial model to those artificial conditions. For example, a surgeon can create a false nose that illustrates what a patient's nose will look like after a surgical procedure. The craniofacial model can then be morphed into a condition that contains the false nose. As such, the patient can be shown before and after models of how their face will look after being effected by surgery. Furthermore, by morphing the craniofacial model into an anticipated future state, a physician can more accurately diagnose the effectiveness of different types of treatment on a patient's problems.

In addition to physical changes caused by surgery or braces, other physiological changes can also be illustrated. For instance, the model of a patient's face can be aged. If the patient is an adult, the age progression will show the onset of wrinkles and a loss of elasticity in the skin. If the patient is a juvenile, the age progression will show growth and maturity of the craniofacial features. In order to change the existing craniofacial model into any theoretical appearance, a final likeliness of that appearance must be added to the database of the model. The craniofacial model can then be easily morphed into that theoretical appearance. The creation of the theoretical appearance can be done by the physician or can be done by a computer artist who is knowledgeable in craniofacial physiology. The use of the model to predict physiological changes is shown by Block 28 in FIG. 1.

It will be understood that the embodiment of the present invention system and method described and illustrated herein are merely exemplary and a person skilled in the art can make many variations to the embodiments shown without departing from the scope of the present invention. All such variations, modifications and alternate embodiments are intended to be included within the scope of the present invention as defined by the appended claims.

What is claimed is:

1. A method of creating a digital computer model of the craniofacial features of a person, comprising the steps of:

scanning the person's external facial features to create a model grid;

photographing the person's external facial features to obtain photo images of the external facial features;

superimposing said photo images onto said model grid, therein creating a first computer model of the person's external facial features;

producing a physical model of the person's teeth;

scanning the physical model of the teeth, therein creating a second computer model of said physical model of said teeth; and integrating said first computer model and said second computer model into a master computer model.

2. The method according to claim 1, further including the step of creating a third computer model of the person's skull.

3. The method according to claim 2, further including the step of integrating said third computer model into said master computer model.

4. The method according to claim 2, wherein said step of creating a third computer model, includes the sub steps of:

generating a generic skull model;

inputting data corresponding to the skull of the person;

altering the generic skull model to correspond to the data corresponding to the skull of the person.

5. The method according to claim 1, wherein said step of scanning the person's external facial features includes providing reference points on at least some of the person's external facial features, and scanning the person's external facial features in a plurality of poses with a laser scanner.

6. The method according to claim 5, wherein said step of photographing the person's external facial features includes taking a plurality of digital photographs of the person's external facial features with said reference points.

7. The method according to claim 6, wherein said step of superimposing said photo imamges onto said model grid includes superimposing said digital photographes onto said model grid using said reference points for alignment.

8. The method according to claim 1, further including the step of creating a bite jig having an orientation plate that extends outside the mouth.

9. The method according to claim 8, further including the steps of:
   scanning the patient's head while biting the bite jig to create a first collection of data points;
   coupling said physical model of said teeth to said bite jig in a subassembly; and
   scanning said subassembly to create a second collection of data points.

10. The method according to claim 9 wherein said step of integrating said first computer model and said second computer model includes orienting said first computer model with said second computer model using said first collection of data points and said second collection of data.

11. A method of creating a three-dimensional computer model of a person's craniofacial features, said method including the steps of:
   providing a first set of reference points on at least some of a person's external facial features;
   scanning the person's external facial features to create a first computer model of the person's external facial features that includes said first set of reference points;
   producing a physical model of the person's teeth;
   creating a second computer model of said physical model of said teeth;
   providing a bit plate having a second set of reference points;
   holding said bite plate in the person's teeth, wherein said second set of reference points protrude from the person's mouth;
   scanning the person while said bite plate is in the mouth, therein producing a reference scan that includes said first set of reference points and said second set of reference points; and
   integrating said first computer model and said second computer model into a master computer model utilizing said first set of reference points and said second set of reference points in said reference scan.

12. The method according to claim 11, further including the step of animating said master computer model by creating a theoretical appearance of craniofacial features and animating said master computer model between modeled craniofacial features and said theoretical appearance.

13. The method according to claim 11, further including the step of animating said master computer model by animating said master computer model to mimic actions selected from a group consisting of chewing, grinning, smiling, growing and aging.

14. The method according to claim 11, further including the step of creating a third computer model of the person's skull.

15. The method according to claim 14, further including the step of integrating said third computer model into said master computer model.

* * * * *